United States Patent [19]

Carroll et al.

[11] Patent Number: 5,027,814

[45] Date of Patent: Jul. 2, 1991

[54] IMPLANTABLE MEDICAL DEVICE EMPLOYING AN IMPROVED WAVEFORM DIGITIZATION NETWORK

[75] Inventors: Kenneth J. Carroll, San Jose; Benjamin D. Pless, Menlo Park, both of Calif.

[73] Assignee: Ventritex, Inc., Sunnyvale, Calif.

[21] Appl. No.: 354,625

[22] Filed: May 19, 1989

[51] Int. Cl.[5] .............................................. A61N 1/00
[52] U.S. Cl. .......................... 128/419 PG; 128/419 D
[58] Field of Search ........ 128/419 D, 419 PG, 419 R, 128/696, 710

[56] References Cited

U.S. PATENT DOCUMENTS

| 4,132,233 | 1/1979 | Hartlaub | 128/419 PG |
|---|---|---|---|
| 4,164,946 | 8/1979 | Langer | 128/419 D |
| 4,295,474 | 10/1981 | Fischell | 128/697 |
| 4,388,928 | 6/1983 | Ekwall et al. | 128/419 PG |
| 4,509,529 | 4/1985 | Money et al. | 128/708 |
| 4,557,266 | 12/1985 | Schober | 128/419 PG |
| 4,571,589 | 2/1986 | Slocum et al. | 128/419 PG |
| 4,773,401 | 9/1988 | Citak et al. | 128/419 PG |
| 4,803,987 | 2/1989 | Calfee et al. | 128/419 PG |
| 4,825,869 | 5/1989 | Sasmor et al. | 128/419 PT |
| 4,858,617 | 8/1989 | Sanders | 128/696 |
| 4,870,974 | 10/1989 | Wang | 128/419 PG |
| 4,873,980 | 10/1989 | Schaldach | 128/419 PG |
| 4,893,362 | 1/1990 | Armington | 128/696 |
| 4,913,145 | 4/1990 | Stotts . | |

OTHER PUBLICATIONS

"All MOS Charge Redistribution Analog-To-Digital Conversion Techniques-Part 1", by James L. McCreary, in *IEEE Journal of Solid-State Circuits*, vol. SC-22, No. 6, Dec. 1975, pp. 113-121.

*Primary Examiner*—William E. Kamm
*Assistant Examiner*—Kennedy J. Schaetzle
*Attorney, Agent, or Firm*—Gerstman & Ellis, Ltd.

[57] ABSTRACT

An implantable medical device includes electrodes coupled to a patient's heart and sensing circuitry having inputs connected to the electrodes for sensing analog cardiac electrical signals from one of the atrial or ventricular channels. The sensing circuitry includes waveform digitization network means for converting the analog atrial or ventricular electrical signals into a parallel output format sign/magnitude digitized output signal.

16 Claims, 4 Drawing Sheets

IMPLANTABLE MEDICAL DEVICE EMPLOYING AN IMPROVED WAVEFORM DIGITIZATION NETWORK

BACKGROUND OF THE INVENTION

This invention relates generally to implantable medical devices and more particularly, it relates to an implantable cardiac defibrillator employing an improved waveform digitization network for converting analog ECG heart signals from the atrium and/or ventricle into a sign/magnitude digitized signal plus a channel identifier bit, which is achieved with very low power consumption and without crosstalk between the channels.

In recent years, there has been substantial progress made in the research and development of defibrillating devices for providing an effective medical response to various disorders, such as ventricular fibrillation. Research effort has also been made toward developing improved sensing techniques for reliably monitoring heart activities so as to determine when a defibrillating high energy shock is required.

One of the techniques of the prior art for determining when ventricular fibrillation is present employs a probability density function, which is implemented with an analog approach. Such a technique, utilizing the probability density function, is disclosed in U.S. Pat. No. 4,202,340 to Langer et al. However, it has been experienced that the prior art probability density function detector can be "triggered" indicating a fibrillation of the heart even when there is a nonlife threatening condition. It has therefore been determined that there is a need for an implantable cardiac defibrillator employing an improved waveform digitization network for distinguishing between malignant tachyarrhythmias, such as ventricular defibrillation, and sinus rhythm.

SUMMARY OF THE INVENTION

It is a general object of the present invention to provide an implantable medical device employing an improved waveform digitization network for processing ECG heart signals from the atrium and/or ventricle channels.

Another object of the present invention is to provide an implantable medical device employing a waveform digitization network for converting analog ECG heart signals from the atrium and/or ventricular channels into a sign/magnitude digitized signal plus a channel identifier bit, which is achieved with very low power consumption and without crosstalk between the channels.

It is still another object of the present invention to provide an implantable cardiac defibrillator employing a waveform digitization network which includes a data converter formed of a binarily weighted switched capacitor array and an operational amplifier, and a control logic device for performing a successive approximation of a sampled analog input voltage on the capacitor array to provide a digitized output signal.

It is still yet another object of the present invention to provide an implantable cardiac defibrillator which includes means for multiplexing of analog atrial signals and analog ventricular signals and a waveform digitization network responsive to the multiplexing means for converting either the analog atrial or ventricular signals into a digitized output signal.

In accordance with these aims and objectives, the present invention is concerned with the provision of an implantable cardiac defibrillator which includes electrodes, sensing circuitry, a charge storing device, and a discharge device. The electrodes are coupled to a patient's heart. The sensing circuitry is provided with inputs connected to the electrodes for sensing analog cardiac electrical signals from one of the atrial or ventricular channels. A charge is stored on the charge storing device. The discharging device is used to deliver a shock to the heart. The sensing circuitry includes a waveform digitization network for converting either the analog atrial or ventricular electrical signals into a sign/magnitude digitized output signal plus a channel identifier bit.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 1:
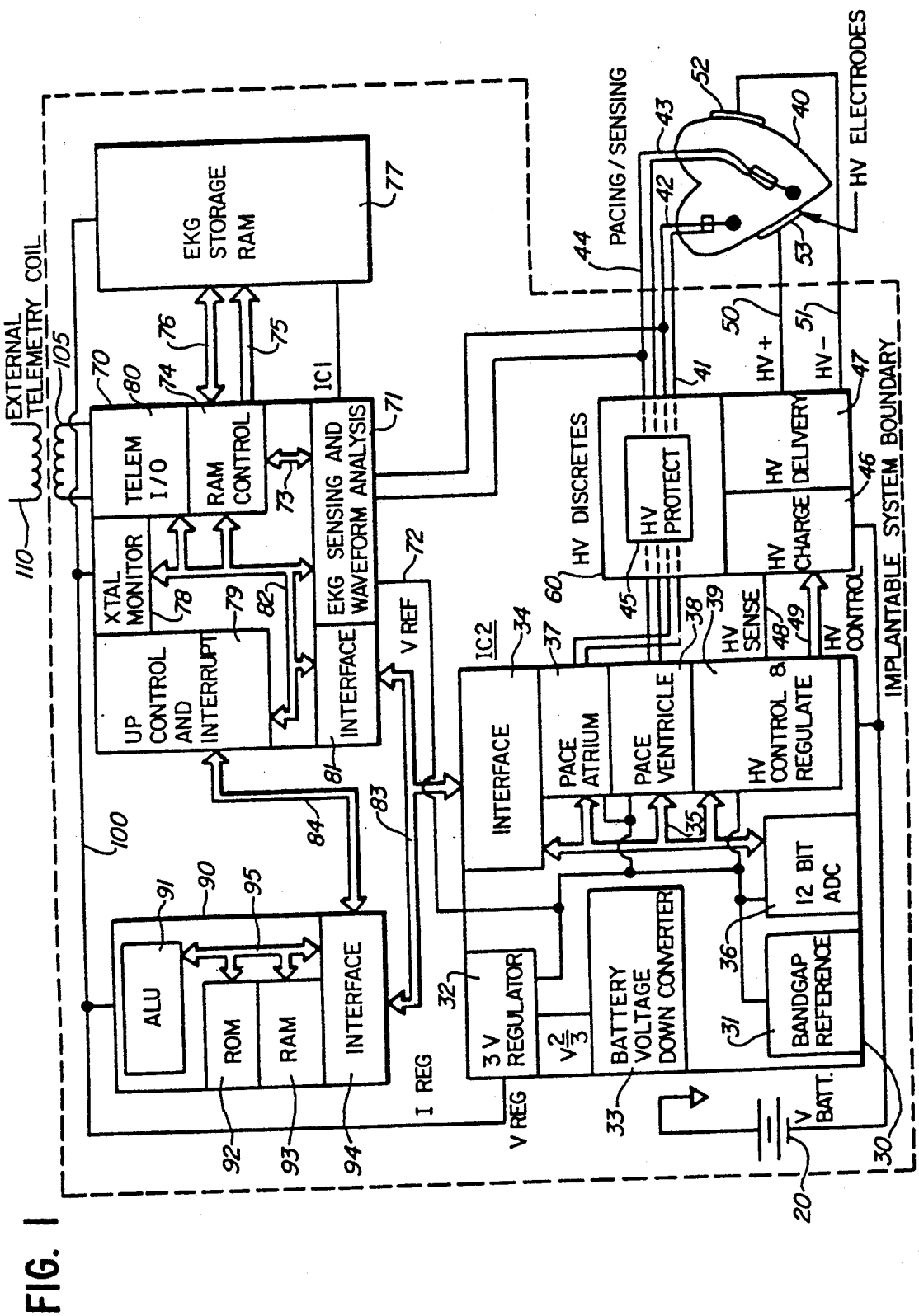
FIG. 1 is a block diagram of an implantable cardiac defibrillator, constructed in accordance with the principles of the present invention.

In FIG. 1, there is illustrated in a functional block diagram format the internal and external elements of an implantable cardiac defibrillator constructed in accordance with the principles of the present invention. A detailed description of the elements of FIG. 1 as well as their interconnection and operation has been presented in co-pending application Ser. No. 344,011 filed Apr. 26, 1989, entitled "Method For Cardiac Defibrillation" and assigned to the same assignee as the present invention, which is hereby incorporated by reference. Thus, the detailed description will not herein be repeated. However, a general description of the elements of FIG. 1 required for an understanding of the present invention will be presented.

In particular, FIG. 1 shows an implantable cardiac defibrillator which includes four integrated circuit chips IC1-IC4 and a set of high voltage discrete component blocks 45-47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42.

The heart signals coming from the ventricle are fed to the block 71 via the line 44.

The block 71 includes a first three-stage amplifier/filter network for sensing the analog heart signals in the atrium and a second three-stage amplifier/filter network for sensing the analog heart signals in the ventricle. The block 71 further includes a waveform digitization network which receives the analog output signals from either the first network or the second network via an analog mutiplexer. The waveform digitization network 10 and the multiplexer 12 utilized in the block 71 are illustrated in detail in FIG. 2 for converting the analog ECG heart signals from the atrium and/or ventricle into a sign/magnitude digitized signal plus a channel identifier bit, which is achieved with very low power consumption and without crosstalk between the channels.

Figure 2:
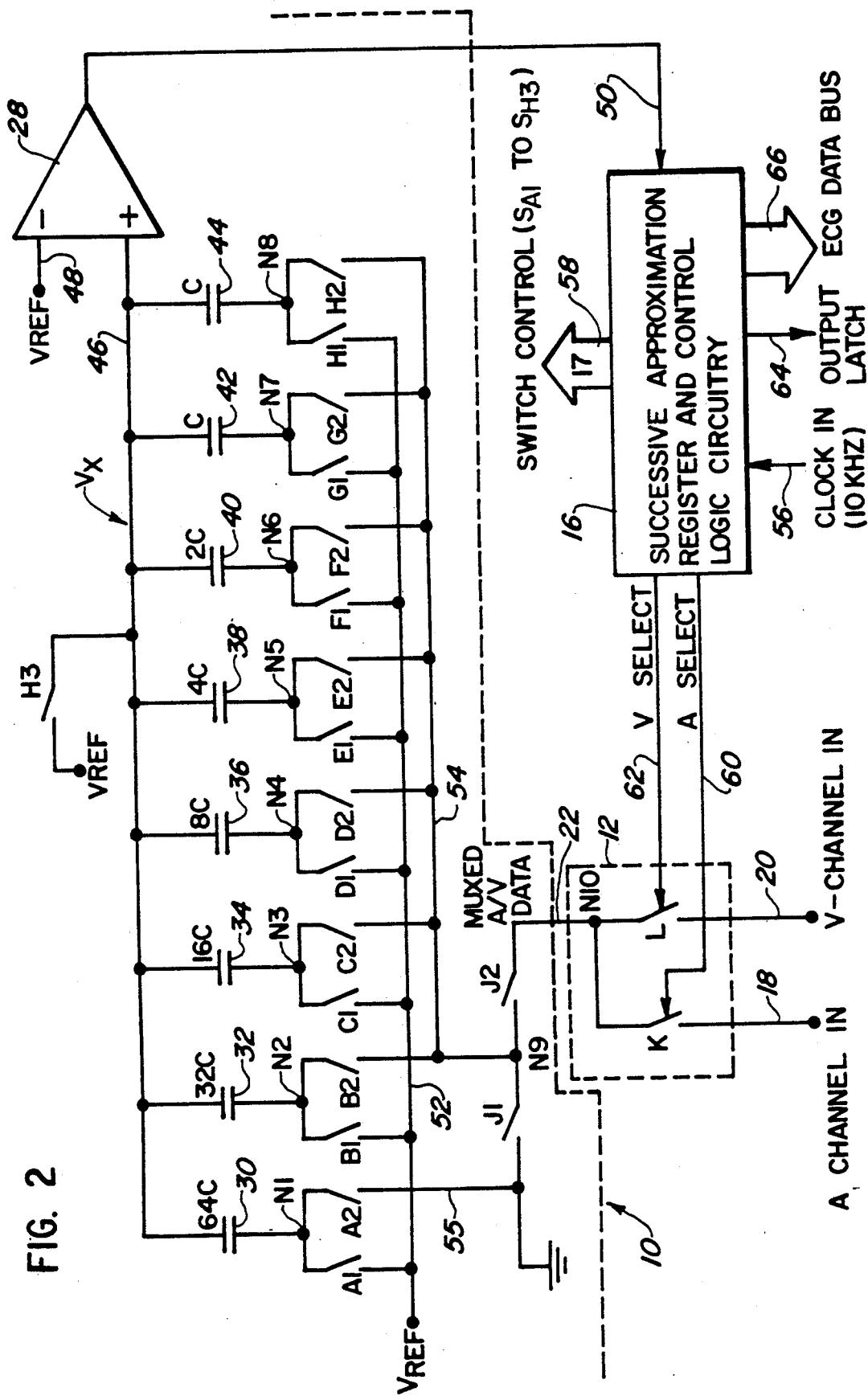
FIG. 2 is a schematic circuit diagram of a waveform digitization network, constructed in accordance with the principles of the present invention.

In FIG. 2, there is illustrated a schematic circuit diagram of a waveform digitization network 10 and an analog multiplexer 12, constructed in accordance with the principles of the present invention. The waveform digitization network 10 is comprised of a data converter 14 and a successive approximation register and control logic circuitry 16. The analog multiplexer 12 receives and inputs the analog ECG heart signals from the atrium on line 18 via the first network of the sensing and waveform analysis block 71 (FIG. 1) and receives the analog ECG heart signals from the ventricle on line 20 via the second network of the block 71. The output of the multiplexer 12 on line 22 corresponds to either the atrial or ventricular heart signals. The input signal on the line 18 is referred to as "A-Channel IN" (atrial heart signal), and the input signal on the line 20 is referred to as "V-Channel IN" (ventricular heart signal). The output signal on line 22 is referred to as "MUXED A/V DATA."

The data converter 14 may be implemented in one of a number of ways. Preferably, the data converter 14 is of the charge redistribution type. The data converter 14 is formed of a binarily weighted switched capacitor array 26 and an analog comparator 28. The capacitor array 26 includes a plurality of rank ordered binarily weighted capacitors 30-44 having capacitance values of 64C, 32C, 16C, 8C, 4C, 2C, C, C, respectively. For purposes of completeness, reference is made to an article entitled "All MOS Charge Redistribution Analog-To-Digital Conversion Techniques—Part 1" by James L. McCreary, in *IEEE Journal of Solid-State Circuits*, Vol. SC-22, No. 6, December, 1975, pp. 113-121. Each of the capacitors 30-44 has its one end or top plate connected together and further joined to the non-inverting input of the analog comparator 28 on line 46. The inverting input of the analog comparator 28 is connected via line 48 to an analog "mid-rail" reference voltage VREF of +1.235 volts, which is the sign bit transition point. The output of the analog comparator on line 50 is connected to an input of the control logic circuitry 16.

Each of the capacitors 30-44 has its other end or bottom plate connected to one of corresponding common nodes N1-N8, respectively. The respective common nodes N1-N8 are connected to a signal input of corresponding switches A1-H1 and also to a signal input of corresponding switches A2-H2. Signal outputs of switches A1-H1 are connected to a first bus line 52 which is connected to the reference voltage VREF. Signal outputs of the switches B2-H2 are connected to a second bus line 54 which is connected to a node N9.

The preferred embodiment of each of the switches is of the standard parallel connection of an N-channel MOS transistor and a P-channel MOS transistor driven by antiphase control signals, this structure is commonly called a transmission gate. For purposes of clarity, the CMOS transmission gates with true and complementary control signals will be schematized as a switch with a single control signal. The node N9 is connected to either an analog ground GND via switch J1 or to the analog input voltage $V_{in}$ on node N10 via switch J2. It will be noted that the signal $V_{in}$ corresponds to the "A-Channel IN" when the switch K of analog multiplexer 12 is closed and the signal $V_{in}$ corresponds to the "V-Channel IN" when the switch L of analog multiplexer 12 is closed. The top plates of the capacitors 30-44 are also connected to a signal output of a switch H3. The signal input of the switch H3 is connected to the reference voltage VREF. The signal output of the switch A2 is connected to the analog ground GND via the line 55.

The control logic circuitry 16 receives, in addition to the output of the analog comparator on the line 50, a clock signal on line 56. The control logic circuitry generates switch control signals SA1-SH3 on a 17-bit bus line 58 for controlling the respective switches A1-H1 and A2-H3. The switches J1 and J2 are controlled by the same signals that control switches H1 and H2 respectively. Further, the control logic circuitry 16 also produces an output signal ASEL on line 60 and an output signal VSEL on line 62 for controlling the analog multiplexer 12. An output latch signal OL is generated on line 64. The output of the waveform digitization network 10 provided from the control logic circuitry 16 onto ECG data bus lines 66 is a 7-bit sign/magnitude (sign bit plus a six-bit magnitude) digitized signal corresponding to a digital representation of the analog input signal $V_{in}$. The 7-bit digitized signal is in a latched parallel output format.

Figure 3:
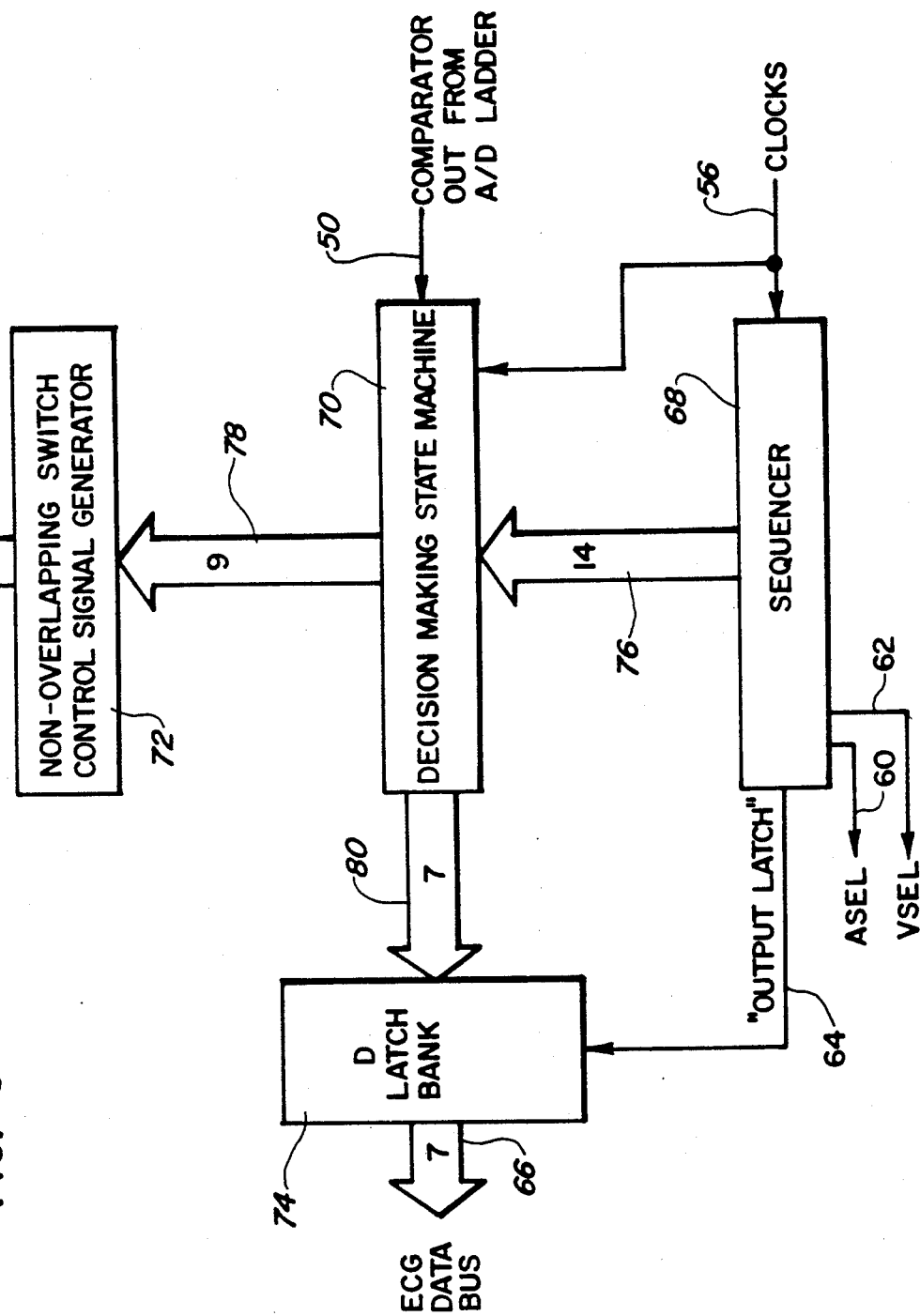
FIG. 3 shows more details, in block diagram form, of the successive approximation register and control logic block of FIG. 2.

In FIG. 3, there is shown in more detail, in block diagram form, the control logic circuitry 16 of FIG. 2. The control logic circuitry 16 is comprised of a sequencer block 68, a decision making state machine block 70, a non-overlapping switch control, signal generator block 72, and a D-latch bank block 74. The sequencer block 68 may be formed of a shift register, which is responsive to the clock signal on the line 56, for generating output logic signals on bus line 76. The decision making state machine block 70 may be formed of logic gates, which are responsive to the output logic signals on the line 76 and the output of the analog comparator on line 50, for generating state signals on line 78 and a plurality of individual data bit signals on line 80. The non-overlapping switch control signal generator block 72 is responsive to the state signals on the line 78 for producing the switch control signals SA1-SH3 which are used to open and close the appropriate switches A1-J2. The D-latch bank block 74 is used to store the individual data bit signals and then responds to the output latch signal OL on line 64 for outputting the 7-bit digitized signal in the parallel format onto the data bus 66.

The operation of the waveform digitization network 10 of FIG. 2 will now be explained with reference to the waveform diagrams of FIGS. 4(a)-4(n). It will be assumed that the analog ECG heart signal from the ventricle is the one desired to be converted to the 7-bit sign/magnitude digitized signal. Therefore, the signal VSEL on the line 62 will be made high, and the signal ASEL on the line 60 will be made low, as shown in respective FIGS. 4(m) and 4(n).

Figure 4:
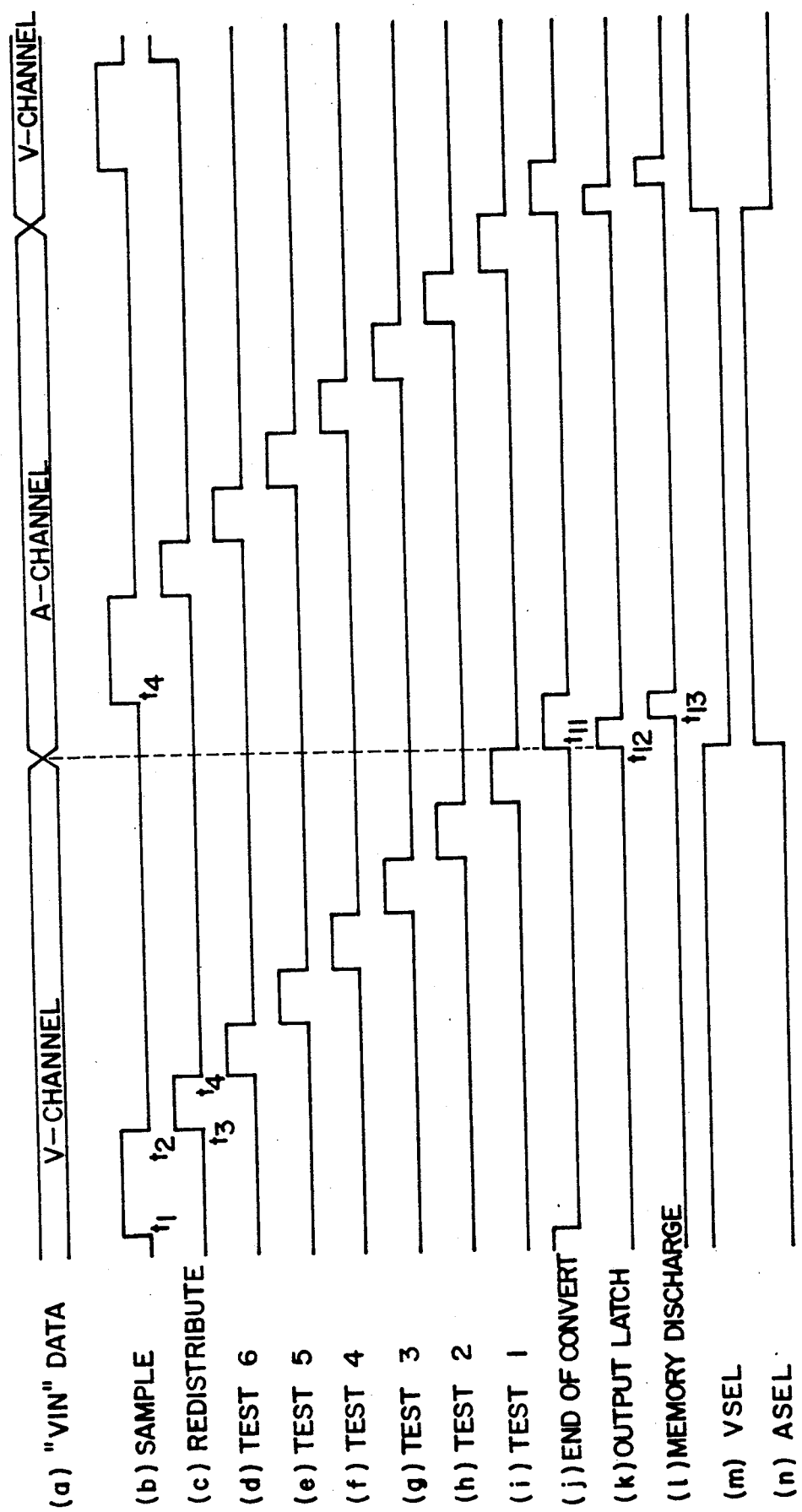
FIG. 4(a)-4(n) are waveforms useful in understanding the operation of the waveform digitization network of FIG. 2.

In order to sample the analog input $V_{in}$ of FIG. 4(a) at the node N10 between the times t1-t2, as shown in FIG. 4(b), the control signal SH2 is made high so as to close the switch J2. The control signals SB2-SH2 are also made high so as to close the corresponding switches B2-H2. This will cause the analog input signal $V_{in}$ to be stored on each of the capacitors 32-44. The control signal SA2 is made high so as to close the switch A2 for connecting the capacitor 30 defining the "sign-bit" capacitor to the ground potential. The control signal SH3 is made high so as to close the switch H3 for connecting the top plates of the capacitors 32-44 to the reference voltage VREF (+1.235 volts). This is referred to as the sampling mode or phase.

Between times t3 and t4, as shown in FIG. 4(c), the input voltage $V_{in}$ is disconnected from the network by opening the switch J2 and the common top plates of the capacitors are disconnected from VREF by opening the switch H3. During this time, the bottom plates of the capacitors 32-44 are connected to the reference, voltage VREF on the line 52 by opening the switches B2-H2 and then closing subsequently the switches B1-J1 in a "break-before-make" fashion. This is referred to as the redistribution mode or phase. As a result, a voltage $V_x$ at the common top plates of capacitors 32-44 will be shifted to a voltage equal to $(3/2)$ VREF—$(\frac{1}{2}) V_{in}$ due to the principle of charge conservation. It is during this redistribution phase that a sign determination is performed.

If the input voltage $V_{in}$ during the sample phase were less than the reference voltage VREF on the line 48, the voltage $V_x$ at the non-inverting input of the operational amplifier will be positive with respect to the reference voltage VREF at the inverting input. Thus, the output of the analog comparator on the line 50 will go to a low logic level which indicates a negative sign of the sampled analog input voltage. The control logic circuitry 16 will be caused to leave the bottom plate of the sign-bit capacitor 30 connected to the analog ground by keeping the switch A2 closed and to set the sign-bit to "one." If the input voltage $V_{in}$ were greater than the reference voltage VREF during the sample phase, the voltage $V_x$ at the non-inverting input of the operational amplifier will be negative with respect to the reference voltage VREF at the inverting input. Thus, the output of the operational amplifier on the line 50 will be changed to a low logic level, which indicates a positive sign of the sampled analog input voltage. The control logic circuitry will cause the sign-bit to be reset to "zero."

At this same time, the control logic circuitry 16 will also cause the bottom plate of the sign capacitor 30 to be switched to the reference voltage VREF by opening the switch A2 and then closing the switch A1. Therefore, irrespective of the sign of the sampled analog input voltage $V_{in}$, the voltage $V_x$ at the common top plates of the capacitors 32-44 will be made to converge on the reference voltage VREF from a higher voltage.

After a sign-bit determination is made, a conventional analog-to-digital conversion utilizing the control logic circuitry 16 is performed. This is referred to as a bit test mode in which each bit is now tested in turn from the most significant bit (capacitor 32) to the least significant bit (capacitor 42). For example, with respect to the capacitor 32, the switch B1 is opened and the switch B2 is closed in the break-before-make fashion thereby connecting its bottom plate to the analog ground via switch J1. The other remaining switches C1-H1 remain closed connecting their bottom plates to the reference voltage VREF. Since the capacitor 32 is the most significant bit, representing one-fourth of the total capacitance in the capacitor array 26, this will reduce the voltage $V_x$ by $(\frac{1}{4})$ VREF.

The comparator 28 compares this $V_x$ with the reference voltage VREF at the inverting input. If the voltage $V_x$ drops below the reference voltage VREF, the output of the analog comparator will be at a low logic level. The control logic circuitry 16 will cause the output bit to be reset to "zero" and the bottom plate of capacitor 30 is reconnected back to the reference voltage VREF, thus reestablishing the pre-bit test state. On the other hand, if the voltage $V_x$ does not drop below the reference voltage VREF, the output of the operational amplifier will remain at a high logic level. The control logic circuitry 16 will leave the capacitor 32 connected to the analog ground and the associated output bit will be set to a "one." This successive approximation process is repeated for the remaining bits until the last bit is completed. As a result, the switch positions of the switches B1-G1 and B2-G2 approximate the digital representation of the analog input signal $V_{in}$. The test signals for this test mode are illustrated in respective FIGS. 4(d)-4(i).

Next, an end-of-convert pulse EOC is generated at time t11 shown in FIG. 4(j) after the testing of the last bit. The pulse EOC will cause the output latch signal OL on the line 64 to be generated for holding the 7-bit data output signal plus the value of the complementary signals VSEL, ASEL, such that a "1" indicates an A-channel conversion and a "0" indicates a V-channel conversion (this constitutes the "channel identifier bit") on the output of the D latch bank block 74. Finally, the pulse MD at time t13 prior to the next sample phase will purge the capacitor array 26 by removing all residual charges. This is accomplished by the control logic circuitry 16 which causes the switches A2, B1-H1, and H3 to become closed. As a result, the sign-bit capacitor 30 is left connected between the reference voltage VREF and the analog ground, and the top and bottom plates of the remaining capacitors 32-44 in the array 26 are connected to the reference voltage VREF.

This is referred to as the memory cancelling phase. This serves to discharge all of the residual capacitor voltages from the just completed conversion. This is necessary because the two independent analog input signals corresponding to the atrium channel and ventricle channel are multiplexed by the analog multiplexer 12 into the waveform digitization network 10 of the present invention in which residual charge from a conversion on one channel can influence the following conversion on the next channel. The memory cancelling phase permits the present digitization network to be shared by two high impedance sources without any crosstalk and without adversely affecting its linearity. If the memory discharge pulse MD were omitted, the output of the first network or second network driving the digitization network would be adversely affected by the residual charge on the capacitor array so as to destroy its linearity.

From the foregoing detailed description, it can thus be seen that the present invention provides an implantable medical device which employs an improved waveform digitization network for converting analog ECG heart signals from the atrium and/or ventricle channels into a sign/magnitude digitized signal plus a sign identifier bit, which is achieved with very low power consumption and without crosstalk between the channels. The waveform digitization network includes a data converter of the charge redistribution type, and a successive approximation register and control logic circuitry.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An implantable medical device comprising:
   electrode means adapted to be coupled to a patient's heart;
   sensing means having inputs connected to said electrode means for sensing analog cardiac electrical signals;
   said sensing means including waveform digitization network means for converting said analog electrical signals into a parallel format digitized output signal; said waveform digitization network means comprising data converter means formed of a binarily weighted switched capacitor array coupled to an input of an analog comparator.

2. An implantable medical device as claimed in claim 1, wherein said waveform digitization network means further comprises control logic means responsive to the output of said analog comparator for performing a successive approximation on a sampled analog electrical signal on said capacitor array to provide the digitized output signal in a latched parallel output format.

3. An implantable medical device as claimed in claim 2, wherein said control logic means includes means for redistributing said sampled input voltage to provide an output sign-bit of the digitized output signal.

4. An implantable medical device as claimed in claim 3, wherein said control logic means further includes means for discharging all of the residual capacitor voltage in said capacitor array after each conversion and prior to the next sample.

5. An implantable medical device as claimed in claim 4, wherein said control logic means includes latch means for providing the digitized output signal in the latched parallel output format.

6. An implantable medical device as claimed in claim 1, wherein said waveform digitization network includes associated switches in said capacitor array, and means for generating switch control signals to switch said associated switches.

7. An implantable medical device as claimed in claim 1, wherein said waveform digitization network includes means for sequentially comparing the voltage on each capacitor of the capacitor array with a reference voltage to provide magnitude bits.

8. An implantable medical device comprising:
   electrode means adapted to be coupled to a patient's heart;
   sensing means having inputs connected to said electrode means for sensing analog cardiac electrical signals;
   means for storing a charge;
   means for delivering a shock to the heart; and
   said sensing means including means for multiplexing of said analog signals and waveform digitization network means responsive to said multiplexing means for converting said signals into a sign/magnitude digitized output signal.

9. An implantable medical device as claimed in claim 8, wherein said waveform digitization network means comprises data converter means formed of a binarily weighted switched capacitor array coupled to an input of an operational amplifier.

10. An implantable medical device as claimed in claim 9, wherein said waveform digitization network means further comprises control logic means responsive to the output of said operational amplifier for performing a successive approximation on a sampled analog electrical signal on said capacitor array to provide the digitized output signal in a latched parallel output format.

11. An implantable medical device as claimed in claim 10, wherein said control logic means includes means for redistributing said sampled input voltage to provide an output sign-bit of the digitized output signal.

12. An implantable medical device as claimed in claim 11, wherein said control logic means further includes means for discharging all of the residual capacitor voltage in said capacitor array after each conversion and prior to the next sample.

13. An implantable medical device as claimed in claim 12, wherein said control logic means includes latch means for providing the digitized output signal in the latched parallel output format.

14. An implantable medical device as claimed in claim 11, wherein said waveform digitization network means includes associated switches in said capacitor array, and means for generating switch control signals to switch said associated switches.

15. An implantable medical device as claimed in claim 11, wherein said waveform digitization network includes means for sequentially comparing the voltage on each capacitor of the capacitor array with a reference voltage to provide magnitude bits.

16. An implantable medical device comprising:
   electrode means adapted to be coupled to a patient's heart;
   sensing means having inputs connected to said electrode means for sensing analog cardiac electrical signals;
   means for storing a charge;
   means for stimulating the heart; and
   said sensing means including waveform digitization network means for converting said analog signals into a sign/magnitude digitized output signal.

* * * * *